(12) United States Patent
Williamson et al.

(10) Patent No.: US 6,239,298 B1
(45) Date of Patent: *May 29, 2001

(54) FUEL LUBRICITY ADDITIVES

(75) Inventors: Will F. Williamson, Seattle, WA (US);
Phillip S. Landis, Alexandria, VA (US);
Blaine N. Rhodes, Bellevue, WA (US)

(73) Assignee: International Lubricants Inc., Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/085,115

(22) Filed: May 26, 1998

(51) Int. Cl.$^7$ .................................................. C07C 59/40
(52) U.S. Cl. .............................. 554/117; 554/25; 554/26; 554/69; 554/221; 554/223; 554/224; 44/385; 44/388; 44/389; 44/393; 44/403; 44/404; 44/418

(58) Field of Search .................................... 554/25, 26, 69, 554/117, 221, 223, 224; 44/385, 388, 389, 393, 403, 404, 418

(56) References Cited

U.S. PATENT DOCUMENTS 5,833,722 * 11/1998 Davies et al. ........................... 44/418
5,858,028 * 1/1999 Davies et al. ........................... 44/393

* cited by examiner

Primary Examiner—Deborah D. Carr
(74) Attorney, Agent, or Firm—Davis Wright Tremaine LLP

(57) ABSTRACT

There is disclosed a fuel lubricity additive, made by a two-step process wherein the first step is co-reacting an unsaturated base oil, predominantly from vegetable oil sources, and a compound having a diene structure and a carboxylic acid group, wherein the second step is esterifying or amidifying the free carboxylic acid group of anhydride group with a poly-hydroxy-containing compound or polyamine compound to form the final fuel lubricity additive useful in diesel fuels. The inventive fuel lubricity additive also is useful as a dispersant.

31 Claims, 3 Drawing Sheets

Figure 3A  Improvement in SLBOCLE Loads with Increasing Concentration of ILI Additives Figure 3B  Improvement in HFRR Scars with Increasing Concentration of ILI Additives

FUEL LUBRICITY ADDITIVES

TECHNICAL FIELD OF THE INVENTION

The present invention provides a fuel lubricity additive, made by a two-step process wherein the first step is co-reacting an unsaturated base oil, predominantly from vegetable oil sources, and a compound having a diene structure and a carboxylic acid group, wherein the second step is esterifying or amidifying the free carboxylic acid group or groups with a poly-hydroxy-containing compound or poly-amine compound to form the final fuel lubricity additive useful in diesel fuels. The fuel lubricity additive formulations and compositions have further utility as dispersants.

BACKGROUND OF THE INVENTION

Beginning in 1993, all highway diesel fuel in the United States was required to have a minimum sulfur content of 0.05% (by weight). Refineries have been able to meet this standard by hydrotreating. Hydrotreating removes sulfur, nitrogen and other metal-bonding reactive sites as well as seal-swelling and lubricating aromatic compounds. However, a major drawback to the hydrotreating process used to reduce sulfur and aromatic levels is that the diesel fuel product has reduced fuel lubricity. The reduced fuel lubricity increases wear rates in many fuel injection systems, as such injections systems have been designed to utilize natural lubricating properties of traditional diesel fuels (typically containing 0.2 to 0.5% by weight sulfur or 2000–5000 ppm). This has caused a dramatic increase in fuel injection system problems manifest as under run and stalling as the most minor to injector nozzle fouling, to fuel pump failures resulting in a need to replace entire systems. This is causing fuel injection systems to be redesigned even as injection pressures have risen to the detriment of wear and mechanical performance.

Distillate petroleum hydrocarbon fractions in the kerosene/diesel fuel range have essentially no lubricity or lubricating value. The high solvent action of the fuel and the constant washing by large volumes of fuel make it impossible to maintain lubricant on pump surfaces. Thus, fuel pumps are subjected to serious wear, leading to pump failure. Fuel compositions have to be treated (formulated) to address wear, erosion and corrosion problems.

Petroleum refineries produce 50 to 60 billion gallons of diesel fuel for consumption in the United States each year. Most refineries are producing only low-sulfur diesel fuels to achieve economies of scale. This means that, even though off-road vehicles are currently exempt from the low-sulfur emission requirements, most, including tractor and other farm equipment, will be using low-sulfur diesel fuels. This will result in increased engine wear in agricultural equipment that was designed for the natural lubricating properties of diesel fuels. The EPA is in the process of developing emission standards for off-road engines which will also cause low-sulfur diesel fuels to be used.

Traditional fuel lubricity additives contain sulfur, phosphorous, zinc, nitrogen or boron. These are called ash forming or catalyst-poisoning additives. Ash forming additives are thermally activated and form sacrificial chemical bonds to metal surfaces. The additive will then "shear" from the metal surface before the metal itself, resulting in protection of the metal surface from wear. Many additives also contribute to particulate emissions during combustion. Moreover, additives can form $SO_x$, $NO_x$ and $PO_x$ emissions, or emissions which can poison a catalyst used in catalytic converters, causing an increase in particulate and hydrocarbon emissions.

Therefore there is a need in the art for diesel fuel additives that impart needed lubricity properties but provide minimal ash or preferably ash-less properties for the purposes of reducing ultimate emissions characteristics. The present invention applies telomer technology to this field of art to provide an improved ashless additive to diesel fuel and kerosene that provides lubricity properties, improved combustion and improved emissions characteristics. The goal, that was achieved by this invention, was to provide a fully fuel-soluble additive molecule, which is derived from renewable sources and contains no ash or deposit-producing elements or catalyst poisons such as sulfur, phosphorous or boron. The invention describes the achievement of that goal.

SUMMARY OF THE INVENTION

The present invention provides a fuel lubricity additive compound, comprising an intermediate adduct of a first moiety reacted in a first reaction with a second moiety to form the intermediate adduct and further esterifying or amidifying the intermediate adduct with a third moiety in a molar ratio of from about 1:2 to about 2:1, wherein the first moiety is an unsaturated triglyceride plant oil or a thermal polymer thereof, wherein the second moiety is a diene or conjugated carbon-carbon double bond acid or anhydride moiety, wherein the first reaction comprises mixing the first moiety with the second moiety in a molar ratio of from about 1:2 to about 2:1 at a temperature of from about 130° C. to about 195° C. under an inert atmosphere; and wherein the third moiety is a polyhydroxy compound or a polyamino compound. Preferably, the unsaturated plant oil is selected from the group consisting of rapeseed oil, tung oil, linseed oil, soya oil, corn oil, peanut oil, canola oil, safflower oil, or combinations thereof. Preferably, the thermal polymer is selected from the group consisting of thermal (telomer) polymers of canola oil, soya oil, linseed oil, corn oil, safflower oil, peanut oil, tung oil, and combinations thereof. Preferably, the second moiety comprises unsaturated compounds having a free carboxylic acid or anhydride group. Most preferably, the second moiety is selected from the group consisting of maleic acid, maleic anhydride, sorbic acid, sorbic anhydride, tetrahydrophthalic anhydride, tetrahydrophthalic acid, salicylic acid, salicylic anhydride, acrylic acid, acrylic anhydride, $C_{1-10}$ alkyl, $C_{2-10}$ alkenyl, or $C_{1-10}$ alkoxy derivatives of the foregoing acids and anhydrides, and combinations thereof. Preferably, the polyhydroxy compound of the third moiety is selected from the group consisting of glycerol, sorbitol, hydroxyquinone, glucose, mannose, 6-carbon sugars, pentose, fructose, 5-carbon sugars, pentaerythritol, catechol, resorcinol, hydroquinone, pyrogallol, 4,4'-dihydroxybiphenyl, 2,4-dihydroxybiphenyl, 2,2'-dihydroxybiphenyl, orthohydroxybenzene, polyhydroxyaromatic compounds having one or two phenyl rings and one or two 5–6 membered aromatic rings having substituted alkyl or alkenyl side chains ($C_{2-10}$) substituted with at least two hydroxyl groups, trimethylolpropane, pentaerythritol, dimethylolpropane, dipentaerythritol, trimethylolethane, ethyleneglycol, polypropyleneglycol, polyethylated alcohols, and combinations thereof. Preferably, the polyamino compound is selected from the group consisting of diethylenetriamine, dimethylenetriarine, dipropylnetriamine, ethyenediamine, propylenediamine, butylenediamine, butylenetriamine, triethylenetetramine, tripropylenetetramine, trimethylenetriamine, tributylenetetramine, tetraethylenepentamine, tetramethylenepentamine, tetrapropylenepentamine, tetraethylenepentamine, tetrabutylenepentamine, hexylenediamine, and combinations thereof. Preferably, the first reaction is conducted under continuous mixing. Preferably, the esterification reaction comprises reaction conditions of from about 150° C. to about 190° C. under an inert atmosphere and further comprises adding an esterification catalyst. Most preferably, the esterification catalyst is an acid catalyst. Most preferably, the esterification catalyst is selected from the group consisting of p-toluene sulfonic acid, hydrophosphorous acid, sulfuric acid, hydrochloric acid, phosphoric acid, acid-activated clays, solid acid catalysts, acidic zeolites, and combinations thereof Preferably, the amidification reaction comprises reaction conditions of from about 130° C. to about 150° C. under an inert atmosphere. Most preferably, the fuel lubricity additive compound is made from the first moiety, second moiety and third moiety compounds selected from the group consisting of in order soya oil-maleic anhydride-sorbitol, soya oil-linseed oil combination-maleic anhydride-sorbitol, soya oil-maleic anhydride-ethylenediamine, and soya oil-maleic anhydride-hydroquinone.

The present invention further provides a process for synthesizing a fuel lubricity additive compound, comprising (a) reacting an unsaturated triglyceride plant oil or a thermal polymer thereof first moiety with a second moiety in a molar ratio of from about 1:2 to about 2:1 at a temperature of from about 130° C. to about 195° C. under an inert atmosphere to form an intermediate adduct, wherein the second moiety is a diene or conjugated carbon-carbon double bond acid or anhydride moiety; and (b) esterifying or amidifying the intermediate adduct with a third moiety in a molar ratio of from about 1:2 to about 2:1, wherein the third moiety is a polyhydroxy compound or a polyamino compound.

Preferably, the unsaturated plant oil is selected from the group consisting of rapeseed oil, tung oil, linseed oil, soya oil, corn oil, peanut oil, canola oil, safflower oil, or combinations thereof Preferably, the thermal polymer is selected from the group consisting of thermal (telomer) polymers of canola oil, soya oil, linseed oil, corn oil, safflower oil, peanut oil, tung oil, and combinations thereof. Preferably, the second moiety comprises unsaturated compounds having a free carboxylic acid or anhydride group. Most preferably, the second moiety is selected from the group consisting of maleic acid, maleic anhydride, sorbic acid, sorbic anhydride, tetrahydrophthalic anhydride, tetrahydrophthalic acid, salicylic acid, salicylic anhydride, acrylic acid, acrylic anhydride, $C_{1-10}$ alkyl, $C_{2-10}$ alkenyl, or $C_{1-10}$ alkoxy derivatives of the foregoing acids and anhydrides, and combinations thereof. Preferably, the polyhydroxy compound of the third moiety is selected from the group consisting of glycerol, sorbitol, hydroxyquinone, glucose, mannose, 6-carbon sugars, pentose, fructose, 5-carbon sugars, pentaerythritol, catechol, resorcinol, hydroquinone, pyrogallol, 4,4'-dihydroxybiphenyl, 2,4-dihydroxybiphenyl, 2,2'-dihydroxybiphenyl, orthohydroxybenzene, polyhydroxyaromatic compounds having one or two phenyl rings and one or two 5–6 membered aromatic rings having substituted alkyl or alkenyl side chains ($C_{2-10}$) substituted with at least two hydroxyl groups, trimethylolpropane, pentaerythritol, dimethylolpropane, dipentaerythritol, trimethylolethane, ethyleneglycol, polypropyleneglycol, polyethylated alcohols, and combinations thereof. Preferably, the polyamino compound is selected from the group consisting of diethylenetriamine, dimethylenetriamnine, dipropylnetriamine, ethyenediamine, propylenediamine, butylenediamine, butylenetriamnine, triethylenetetramine, tripropylenetetramine, trimethylenetriamine, tributylenetetramine, tetraethylenepentamine, tetramethylenepentamine, tetrapropylenepentamine, tetraethylenepentamine, tetrabutylenepentamine, hexylenediamine, and combinations thereof. Preferably, the first reaction is conducted under continuous mixing. Preferably, the esterification reaction comprises reaction conditions of from about 150° C. to about 190° C. under an inert atmosphere and further comprises adding an esterification catalyst. Most preferably, the esterification catalyst is an acid catalyst. Most preferably, the esterification catalyst is selected from the group consisting of p-toluene sulfonic acid, hydrophosphorous acid, sulfuric acid, hydrochloric acid, phosphoric acid, acid-activated clays, solid acid catalysts, acidic zeolites, and combinations thereof. Preferably, the amidification reaction comprises reaction conditions of from about 130° C. to about 150° C. under an inert atmosphere.

The present invention provides a diesel fuel composition having a fuel lubricity additive compound, comprising a diesel fuel and from about 50 ppm to about 5000 ppm of a fuel lubricity additive, wherein the fuel lubricity additive comprises an intermediate adduct of a first moiety reacted in a first reaction with a second moiety to form the intermediate adduct and further esterifying or amidifying the intermediate adduct with a third moiety in a molar ratio of from about 1:2 to about 2:1, wherein the first moiety is a unsaturated triglyceride plant oil or a telomerized polymer thereof, wherein the second moiety is a diene or conjugated carbon-carbon double bond acid or anhydride moiety, wherein the first reaction comprises mixing the first moiety with the second moiety in a molar ratio of from about 1:2 to about 2:1 at a temperature of from about 130° C. to about 195° C. under an inert atmosphere; and wherein the third moiety is a polyhydroxy compound. Preferably, the unsaturated plant oil is selected from the group consisting of rapeseed oil, tung oil, linseed oil, soya oil, corn oil, peanut oil, canola oil, safflower oil, or combinations thereof Preferably, the thermal polymer is selected from the group consisting of thermal (telomer) polymers of canola oil, soya oil, linseed oil, corn oil, safflower oil, peanut oil, tung oil, and combinations thereof Preferably, the second moiety comprises unsaturated compounds having a free calboxylic acid or anhydride group. Most preferably, the second moiety is selected from the group consisting of maleic acid, maleic anhydride, sorbic acid, sorbic anhydride, tetrahydrophthalic anhydride, tetrahydrophthalic acid, salicylic acid, salicylic anhydride, acrylic acid, acrylic anhydride, $C_{1-10}$ alkyl, $C_{2-10}$ alkenyl, or $C_{1-10}$ alkoxy derivatives of the foregoing acids and anhydrides, and combinations thereof Preferably, the polyhydroxy compound of the third moiety is selected from the group consisting of glycerol, sorbitol, hydroxyquinone, glucose, mannose, 6-carbon sugars, pentose, fructose, 5-carbon sugars, pentaerythritol, orthohydroxybenzene, polyhydroxyaromatic compounds having one or two phenyl rings and at least two hydroxyl groups (e.g., having a phenyl moiety substituted in any of the foregoing polyhydroxy compounds), trimethylolpropane, polyethoxylated alcohols, and combinations thereof Preferably, the polyamino compound is selected from the group consisting of diethylenetriarine, dimethylenetriamine, dipropylnetriamine, ethyenediamine, propylenediamine, butylenediamine, butylenetriamine, triethylenetetramine, tripropylenetetramine, trimethylenetriamine, tributylenetetramine, tetraethylenepentamine, tetramethylenepentamine, tetrapropylenepentamine, tetraethylenepentarnine, tetrabutylenepentamine, hexylenediarnine, and combinations thereof Preferably, the first reaction is conducted under continuous mixing. Preferably, the esterification reaction comprises reaction conditions of from about 150° C. to about 190° C. under an inert atmosphere and further comprises adding an esterification catalyst. Most preferably, the esterification catalyst is an acid catalyst. Most preferably, the esterification catalyst is selected from the group consisting of p-toluene sulfonic acid, hydrophosphorous acid, sulfuric acid, hydrochloric acid, phosphoric acid, acid-activated clays, solid acid catalysts, acidic zeolites, and combinations thereof Most preferably, the fuel lubricity additive compound is made from the first moiety, second moiety and third moiety compounds selected from the group consisting of in order soya oil-maleic anhydride-sorbitol, soya oil-linseed oil combination-maleic anhydride-sorbitol, soya oil-maleic anhydride-ethylenediamine, and soya oil-maleic anhydride-hydroquinone.

A fuel lubricity additive or a dispersant comprising the product of a first and a second reaction, (a) wherein the first reaction is an adduction reaction of a base oil and a dienophile having a carboxylic acid moiety selected from a formula I or a formula III:

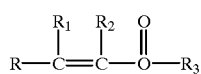

I wherein R, $R_1$ and $R_2$ are independently hydrogen, hydroxyl, a straight chain or branched chain $C_{1-12}$ alkyl, $C_{1-12}$ acyl, $C_{1-12}$ aryl, $C_{4-12}$ cycloalkyl, or $C_{1-12}$ alkoxy; and wherein $R_3$ is hydrogen, a straight chain or branched chain $C_{1-12}$ alkyl, $C_{1-12}$ acyl, $C_{1-12}$ aryl, $C_{4-12}$ cycloalkyl, or $C_{1-12}$ alkoxy, or formula II

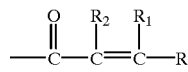

II or formula III

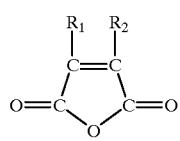

III wherein $R_1$ and $R_2$ are the same as in formula I; and (b) wherein the second reaction is an esterifying or an amidifying of the carboxylic acid functional moiety of the aliphatic intermediate product of the first reaction with a polyol compound or polyamino compound having from 2 to 10 free hydroxyl groups and selected from the group consisting of substituted or unsubstituted mono-, di-, tri-, tetra- or penta-sugars, glycerols, glycols, pentaerythrols, and combinations thereof, wherein the substitutions are selected from the group consisting of hydroxyl, oxo, halogen (chloro, bromo, iodo, fluoro), straight chain or branched chain $C_{1-12}$ alkyl, $C_{1-12}$ acyl, $C_{1-12}$ aryl, $C_{4-12}$ cycloalkyl, hydroxyl, and $C_{1-12}$ alkoxy. Pr the dienoid carboxylic acid is selected from the group consisting of maleic acid, sorbic acid, acrylic acid, and combinations thereof.

Preferably, the base oil is selected from the group consisting of HEAR (high erucic acid rapeseed oil), linseed oil, soybean oil, canola oil, telomer oil having a kinematic viscosity of 6000 SUS, and combinations thereof Preferably, wherein the base oil is either a triglyceride (all straight chain) with at least one of the acyl chains being unsaturated, or a straight chain wax ester of from about 18–48 carbons atoms in length and being at least monounsaturated. Most preferably, the base oil acyl fatty acid chains of the triglyceride are from 3 to 24 carbon atoms in length (straight) and have from one to three double bonds. Most preferably, the base oil unsaturated fatty acid acyl chains have from 10–24 carbons atoms.

DETAILED DESCRIPTION OF THE INVENTION

Synthetic Process

Figure 1:
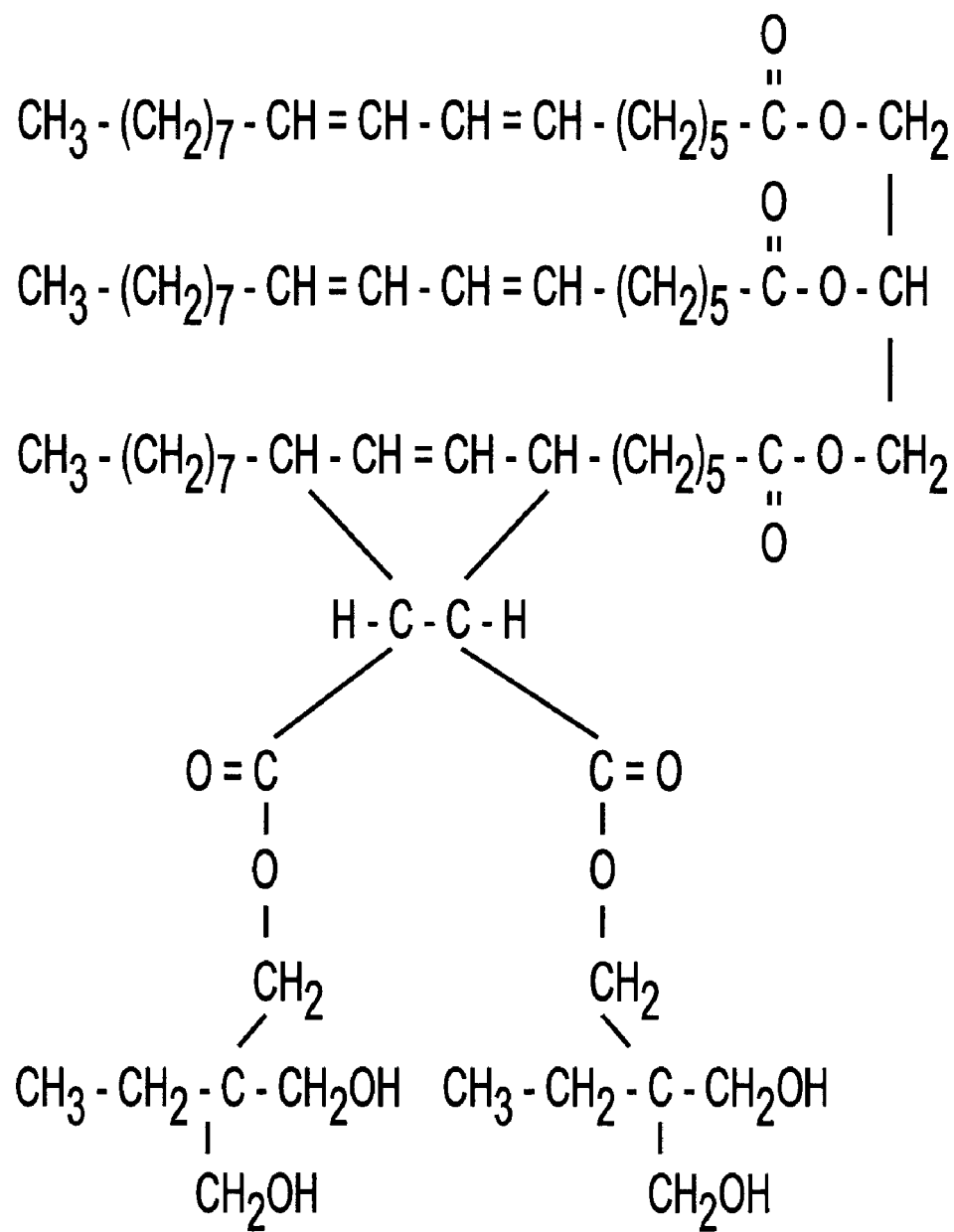
FIG. 1 shows a chemical structure of the product of a reaction between an unsaturated fatty acid and a dienoid adduct and then further esterification or amidification. Specifically, the structure shown in FIG. 1 is the reaction product, according to the present invention, of HEAR (high erucic acid rapeseed oil), maleic anhydride and trimethylolpropane.
Figure 2:
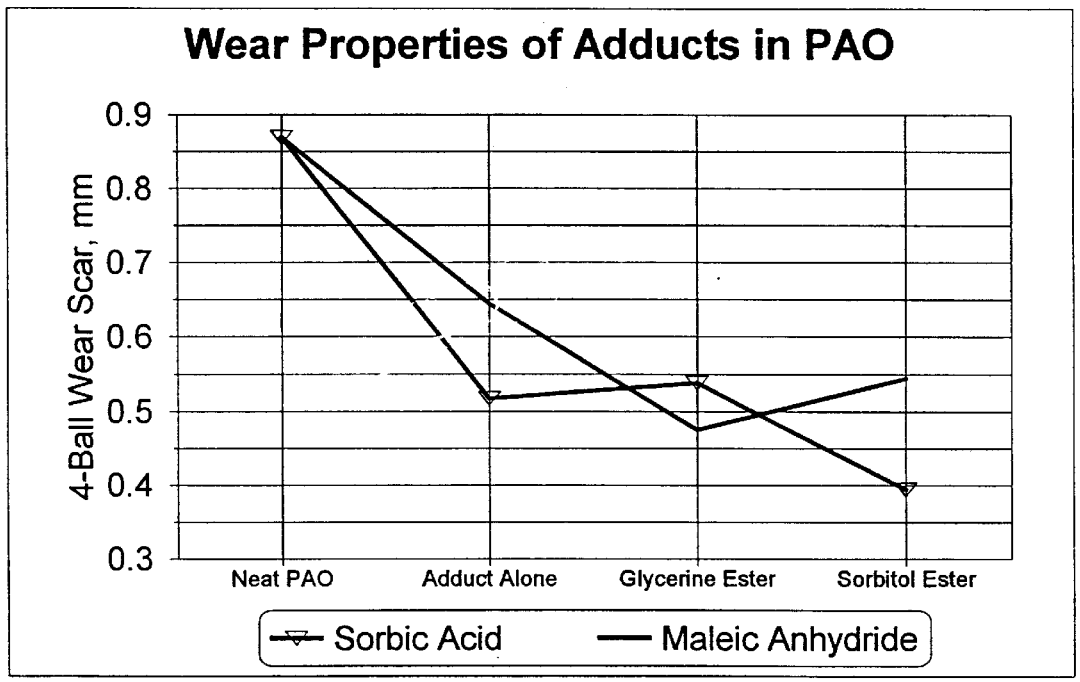
FIG. 2 shows the results of a 4 ball wear test of rapeseed oil as the base oil, maleic anhydride or sorbic acid as a carboxylic acid-containing adduct and sorbitol or glycerine as the esterified polyol. These data shown are for low viscosity polyalphaolefin (POA, a synthetic paraffinic oil with no sulfur), which can serve as an extreme model of hydrotreated diesel oil. Moreover, addition of the inventive additive (5% by weight) provided significant antiwear properties to PAO as measured by decreased wear scar size.
Figure 3:
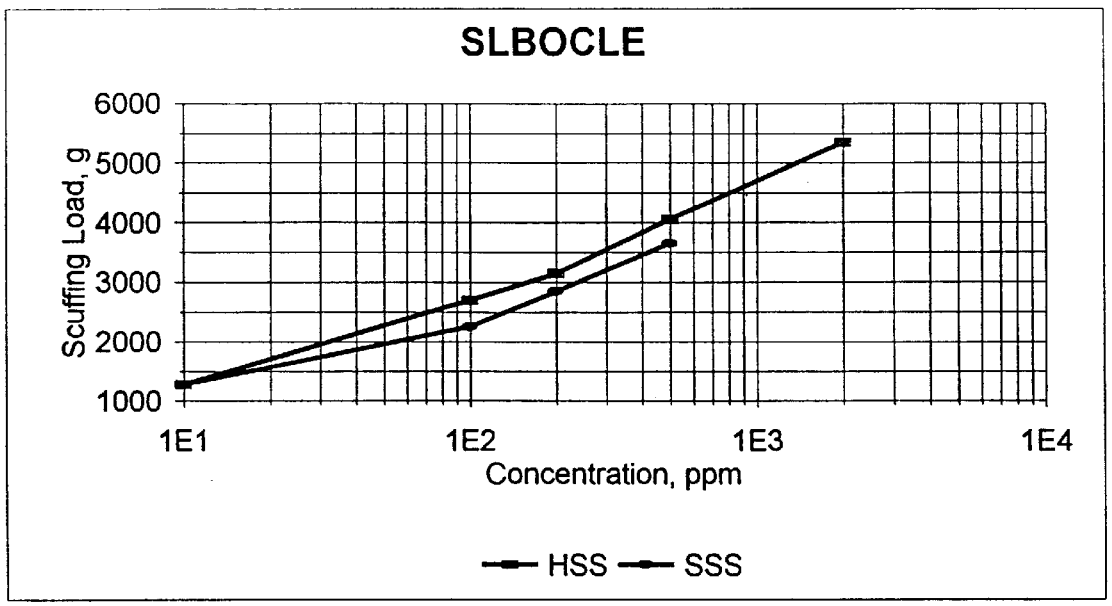
FIG. 3A shows improvement in SLBOCLE loads with increasing concentrations of HEAR-sorbic acid-sorbitol and soy oil-sorbic acid-sorbitol additives at the concentrations noted.
FIG. 3B shows improvement in HFRR scars with increasing concentration of the same additives.
Figure 3:
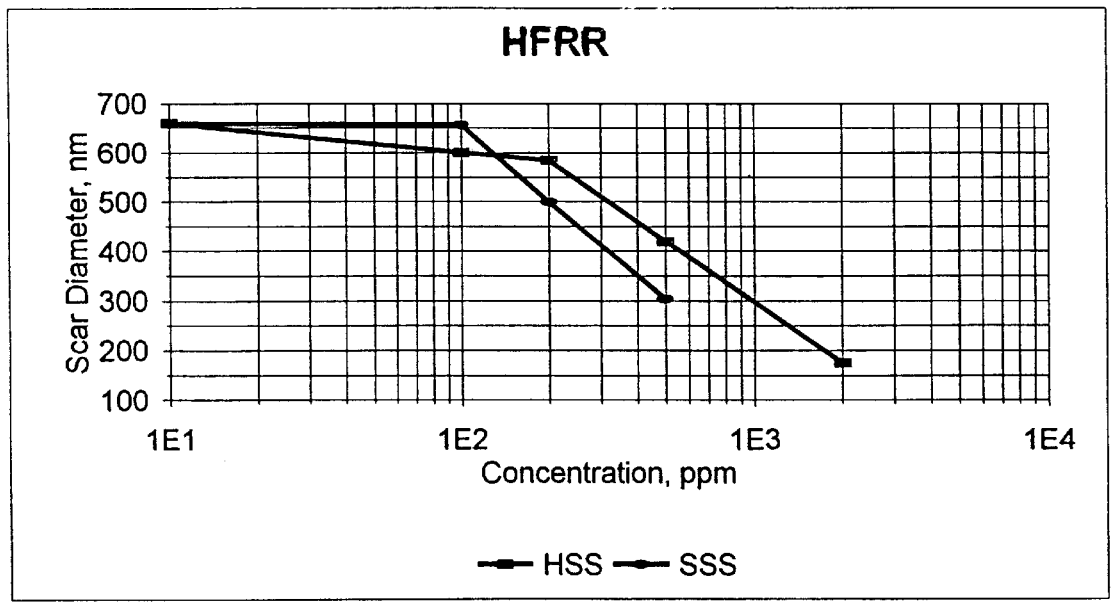

The synthetic process for the production of the inventive dispersants is a two-step process. The first step reacts the triglyceride with a dieneophile in a Diels-Alder reaction. This first step is an adduction reaction accomplished by reacting an unsaturated site of an unsaturated triglyceride oil, such as HEAR, with a dieneophile having conjugation of the double bonds and carboxylic acid group. Examples of the dieneoids are maleic anhydride, acrylic acid, sorbic acid, and ascorbic acid (vitamin C). All of the adducts are characterized by having a conjugated double bond moiety that is not sterically hindered for the Diels-Alder reaction and a free carboxylic acid moiety available for reaction in the second process step.

The Diels-Alder reaction is initiated, for example, by mixing the unsaturated triglyceride and the dieneophile on a 1:1 molar basis and adding a small amount (0.5% to 5% by weight of the dienophile)of di-t-butylperoxide and heat (range of 120° C. to 180° C.). The Diels Alder reaction proceeded until there was no further evolution of vapor phase of water, butanol (from the catalyst di-t-butylperoxide) and unreacted adduct component. The results of the first reaction step using HEAR as the unsaturated triglyceride and either styrene, maleic anhydride, acrylic acid or sorbic acid at various molar ratios is provided in Table 1.

TABLE 1

| dieneophile | molar ratio copolymer:H EAR | exotherm, max delta, °C. | acid number | iodine number | % complete (calculated) |
|---|---|---|---|---|---|
| maleic anhydride | 0.5:1 | 9 | 24.6 | 74.7 | 100 |
| maleic anhydride | 1:1 | 24 | 65.9 | 58.7 | 85 |
| acrylic acid | 1:1 | liquid addition | 100 | 66.3 | 100 |
| sorbic acid | 1:1 | <5 | 32.0 | 95.0 | 62 |

The second step reacts the carboxylic acid moiety on an aliphatic ring intermediate with either a polyol or polyamine polar reactant (in a esterification or amidification reaction, depending upon the reactant) to form final products that are dispersants or diesel fuel lubricity additives. Illustrative polyols include glycerol (three hydroxyl groups) and the sugar derivative sorbitol with six chiral hydroxyl groups. Illustrative polyamines included ethylenediamine (EDA) having two amine moieties and tetraethylene pentamine having five amine groups. The second reaction step was carried out in the presence of hypophosphorous acid (and could also include, for example, solid acids such as silica gel, alumina or acid-activated clays, or combinations thereof) and an optional esterification catalyst (preferably at the lower reaction temperatures) at a temperature within the range of from about 150° C. to about 230° C.

The Diels-Alder reaction products that retained acid functionality were the base stocks for ester and amide reactions used to add functional, polar compounds to the acid site that resulted in anti-wear properties. The second process step comprises a reaction of the active carboxylic acid site on the intermediate product with polyols or polyamines to form the anti-wear products. Two each of the polyols and polyamines were chosen to illustrate the breadth of the chemistry involved. The first example represents a few active sites and the second example represents many active sites. Glycerine (three hydroxyls) and ethylenediamine (EDA) (two amine groups) were chosen as having few active sites on a polyol and a polyamine, respectively. Sorbitol (six hydroxyls) and tetraethylene pentamine (five amine groups) were used as the reagents having many active sites.

The second process step comprises a reaction of the active carboxylic acid site on the intermediate product with polyols or polyamines to form dispersant products or with hydroquinone to form antioxidants. Two each of the polyols and polyamines were chosen to illustrate the breadth of the chemistry involved. The first example represents a few active sites and the second example represents many active sites. Glycerine (three hydroxyls) and ethylenediamine (EDA) (two amine groups) were chosen as having few active sites on a polyol and a polyamine, respectively. Sorbitol (six hydroxyls) and tetraethylene pentamine (five amine groups) were used as the reagents having many active sites.

The resulting copolymers were tested and characterized for determination of the best molar ratio for use in the second step of the synthesis as well as for reference. The results are presented in Table 2.

TABLE 2

| Adduct | Mole Ratio | Specific Gravity | Viscosity Data | | | 20% Solubility Data | | |
|---|---|---|---|---|---|---|---|---|
| | | | 40 C | 100 C | VI | MVI 100 N | Canola Oil | PAO |
| HEAR | NA | 0.92 | 35 | 7 | 210 | Yes | Yes | No |
| Maleic Anhydride | 0.5:1 | .942 | 244.9 | 31.9 | 174 | Yes | Yes | Yes |
| | 1:1 | 1.01 | 3460 | 173.2 | 152 | Yes | Yes | Yes |
| | 1.25:1 | Semi Solid at 40 C | | 2892 | NA | Yes | Yes | No |
| Acrylic Acid | 0.5:1 | 0.94 | 156.4 | 23.5 | 181 | Yes | Yes | Yes |
| | 1:1 | 0.947 | 652.4 | 65.7 | 174 | Yes | Yes | No |
| | 2:1 | Competing acrylic polymerization reaction controls | | | | | | |
| Styrene | 1:1 | 0.906 | 84.7 | 15.0 | 187 | Yes | Yes | Yes |
| | 2:1 | 0.939 | 166.4 | 30.4 | 226 | Yes | Yes | No |
| | 3:1 | 0.941 | Competing styrene polymerization reaction controls | | | | | |
| Sorbic Acid | 0.6:1 | .911 | 117.6 | 16.0 | 145 | Yes | Yes | Yes |

The reaction of the polyols was carried out in the presence of hypophosphorous acid, an esterification catalyst, at temperatures in the range of 170–230° C. Glycerine was added as a pure liquid and the reaction continued until the water ceased to boil off. Sorbitol was added as a solid and heated to 230° C. under a nitrogen atmosphere in the presence of catalyst. The resulting sorbitol ester products were not clear and considerable unreacted sorbitol was filtered out of the solution. The filtration process was made difficult because of the high viscosity of the polyol products.

The polyamines were liquid and added slowly to the heated intermediates. Temperatures of the reactions ranged between 150° C. and 180° C. with exotherms of 30° C. for ethylenediamine and 10° C. for tetraethylene pentamine. No catalyst was necessary for the amide reaction. The product were amine waxes that ranged from solid in the case of the ethylenediamine products to viscous fluids in the case of tetraethylene pentamine. All the amine products were filtered hot to remove solid reaction by-products.

A summary of the process observations for making the polar products and product chemical properties are presented in Table 3.

TABLE 3

Process Results of Polar Product Manufacture

| Adduct | Polar Reactant | Exotherm Process | Acid Number | Viscosity cps @ 100 C | % Reacted (calculated) |
|---|---|---|---|---|---|
| Maleic Anhydride | Glycerine | Liquid addition | 6.7 | 156 | 82 |
| | Sorbitol | Difficult to filter | 5.7 | 128 | 86 |
| | EDA | 50 C-Medium wax | N/A | 197 | N/A |
| | TEPA | Uncontrollable polymerization | N/A | N/A | N/A |
| Acrylic Acid | Glycerine | Liquid addition | 7.3 | 21.7 | 71 |
| | Sorbitol | Filtration required | 8.6 | 21.3 | 71 |
| | EDA | 30 C-Hard wax | N/A | 720 | N/A |
| | TEPA | 10 C-Semi solid fluid | N/A | 400 | N/A |
| Sorbic Acid | Glycerine | Liquid addition | 7.1 | 21.2 | 48 |
| | Sorbitol | Filtration required | 6.8 | 19.0 | 49 |
| | EDA | 30 C-Medium wax | N/A | 117 | N/A |
| | TEPA | 10 C-Viscous fluid | N/A | 115 | N/A |

Adduction of vegetable oils and dieneophiles with conjugated double bonds results in several structures via the same general reaction mechanism. The Diels-Alder reaction is the best example of the mechanism, but even if the reactant is not specifically a dieneophile, such as maleic anhydride or acrylic acid, an intermediate ring structure of 4, 5, or 6 carbon atoms was produced.

The presence of this ring structure and the presence of the reactants that were chemically added to it in the following ester/amide reaction was confirmed by Fourier Transform Infrared (FTIR) spectrophotometry. FTIR reveals the types of organic chemical bond structures by their absorption of energy in the infra red wavelengths (2.5–20 micro meters). High absorption of radiation at a particular wavelength reveals many of a particular bond in the sample. The lowest point of the spike is the reference wave number of the absorption.

All of the FTIR spectra for the adduct products show the aliphatic ring peaks at 1000 and 900 cm$^{-1}$ indicating that the reaction proceeded according to the expected mechanism. Furthermore, all the spectra showed the carbonyl (C=O) absorption at 1750, although the peak was weakened considerably and adopted to lower wavelengths, typical of amide linkages. The polyol and hydroquinone products showed a hydroxyl (O—H) peak at 3500 and the polyamines the N—H peak at 3200 as expected showing that these products contained at least some of the reactants.

Dispersency

The first requirement for determining dispersency is to determine a test to show differentiation of the materials in the three oils being tested. The procedure involved a 0.2% level of candidate additive was dissolved in each basestock and then a fixed level of ~0.5% fumed carbon black (lamp black) was dispersed in the mixture. The materials were all tested in a controlled temperature oven at 100° C. for consistency and to expedite settling. The temperature of the oil and the temperature of the oven being equal minimized convection flow in the oil stirring the particulates. Measurement of the residual suspended carbon in the oil over a set settling time is a measure of the dispersency of the fluid.

A straight side tube was prepared, using a Kimax tube Art No: 32501, a gallon jug lid drilled for ¼ inch rod and for syringe access, a ¼" OD polished steel rod, a 10 ml glass syringe, and a rubber stopper. An oven was preheated to 100° C., and 99.8 g of base stock plus 0.2 g of sample were placed in a 150 ml beaker. A charge of 0.5 g carbon black was added to the oil and the mixture was heated and stirred on a hot plate with 1.5 inch stirring bar at speed 1 to 2 for 10 min while heating to 100° C. Using the glass syringe, a 10 ml sample was pulled for sediment from the top of the agitated beaker just before charging to the settling tube. A straight sided tube was filled to the bottom of the KIMAX labeling, and the filled tube was placed into the oven. The first 10 ml sample, as per ASTM D 4807, was filtered with 56 mm Whatman 934AH glass microfiber filter media, and 56 mm Whatman 41 analytical ashless filter paper. At assigned intervals, samples were pulled using a clean glass syringe and filtered as described above. When the samples no longer showed significant change in the solids content, the lid and rod are carefully removed as a unit from the tube. The rod was allowed to dry in the oven draining onto a drip pan for 24 hours before examining. The carbon deposition pattern on the polished steel rod was recorded.

Samples were taken and analyzed for dispersed carbon at the start of the test, after two hours, and after 23 hours of settling, for each of the dispersant candidates in canola oil, MVI 100 N and 2 cSt PAO base stocks. Included in the study as references were samples of each of the base stocks without additives (NEAT), with 0.2% HEAR oil as a dispersant, a widely recognized commercial lubricant dispersant, a standard, mineral oil based engine oil and a synthetic based engine oil. Successful candidate dispersants were found to have settling profiles similar to the commercial dispersant and much slower than the NEAT base stock.

These data from each base stock was ranked by 2 hour results and by 23 hour results. In general, there was not a significant difference between the rankings at the two sampling times, especially in the ranks of strong dispersants. There were some surprises when a few of the products turned out to be effective coagulants that flocculated the carbon black and settled it quickly from the liquid. Finally, cross studies on concentration were conducted to determine if any of the coagulants became dispersants at different concentrations.

In canola oil, only the maleic anhydride-glycerine product performed as well as the commercial reference material for dispersency. The NEAT canola oil was not a good dispersant for the carbon black and the products that did not improve the dispersency stayed very close to the NEAT fluid in settling rates. The additives showed the following order of dispersant effectiveness: maleic anhydride>sorbic acid>acrylic acid and the polyols out-performed the polyamines. The study of reactive sites showed that few sites were more effective than many in every case. Finally, lowering the concentration of the ethylenediamine adduct of the maleic anhydride/HEAR copolymer by two orders of magnitude did not change the dispersency significantly.

The NEAT MVI 100N oil was very effective at dispersing and holding the carbon in suspension all by itself. The commercial dispersant, the MVI 100N with 0.2% HEAR, and the complete motor oil were equivalent. Only one of the candidates, the sorbitol/maleic anhydride/HEAR, was not actually harmful to the dispersency of this base stock. On the other hand the tetraethylene pentamine products showed the greatest coagulant properties in the mineral oil, with polyamines generally showing strong coagulant properties and polyols not having much effect either way. The concentration of the tetraethylene pentamine/sorbic acid/HEAR product was varied upward and it coagulated more effectively at low concentrations, but reducing the level of ethylenediamine/maleic anhydride/HEAR, another coagulant, caused the dispersency to approach the NEAT line.

The NEAT PAO showed the poorest dispersency except for the coagulants. The polyol products of maleic anhydride were the most effective dispersants of the candidates made. They were not equal to the synthetic motor oil or the commercial dispersant tested, but were 2 orders of magnitude over the values of the NEAT base stock. Again, the polyols tended toward being dispersants and the polyamines, especially the tetraethylene pentamine materials, were effective coagulants. The effect of active sites showed improvement with number in maleic anhydride or sorbic acid polyols. All other products became coagulants as the number of active sites goes up. A study of dispersency with the concentration of the tetraethylene pentamine adduct of sorbic acid/HEAR, showed little difference down to 20 ppm. At that point, a small dispersency was established. Ethylenediamine in maleic anhydride/HEAR did not show any increase in dispersency as the concentration was reduced.

The steel rods from each dispersion sample were evaluated. The expected result was multiple bands of uniform deposits, increasing in thickness with depth. The rod was present as the suspension was introduced, and then, as the level changed incrementally by sampling, only the part of the rod still in the liquid would pick up more carbon deposits. The reason for this rod was to make certain that a candidate did not show high dispersency and yet cause all of the carbon to deposit on steel surfaces. A rod would show this by a series of shaded bands, getting darker the longer that part of the rod was exposed to the suspension. This part of the experiment showed that such a concern was unfounded.

The darkest steel rod, showing the most distinct bands, belonged to the mineral oil based engine oil. The other samples were faint and had to be evaluated by reflected light at an oblique angle. The deposits were of four types: Multiple bands of a uniform shade each, a single shade down the entire rod, a single gradient, lighter to darker up or down the rod, and gradients in each band of multiple bands. The relative shade ranged from none discernible, very light (LL), light (L), medium (M), dark medium (DM), and dark (D). Even the "dark" samples were not very heavy in deposits after 23 hours. The distribution of the small sample population is generally normal, tending toward between Light and Medium. Individually, the PAO tended to have more occurrences of the median shades, the MVI 100N next, and the canola oil a flatter, more diverse group.

These dispersency studies showed that the polyols esters of the maleic anhydride/HEAR copolymer are the most efficient dispersants. They also showed properties of coagulation in an oil system that may be useful in oil recycle and filtration.

Emulsion Characteristics

Demulsibility and water mixture characteristics of the products in a MVI 100N were studied 20 as an indicator of detergency. An adduct product was dissolved in the MVI 100N at 0.2% by weight and the solution mixed 50:50 by volume with water. The mixture was emulsified in a high speed blender and allowed to separate in a glass cylinder. The results are presented in Table 4.

TABLE 4

Emulsion Characteristics of Adducts

| Adduct | Polar Reactant | Concentration | Emulsion @ 12 Hours |
|---|---|---|---|
| Control | N/A | 100% MVI 100N | Complete water separation 2 mm oil separation from WIO emulsion |
| Maleic Anhydride | Glycerine | 0.2% | Same as Control |
| Acrylic Acid | Glycerine | 0.2% | Same as Control |
| Sorbic Acid | Glycerine | 0.2% | Same as Control |
| Maleic Anhydride | Sorbitol | 0.2% | 1/2 water volume separation No oil separation from WIO emulsion |
| Acrylic Acid | Sorbitol | 0.2% | 1/2 water volume separation No oil separation from WIO emulsion |
| Sorbic Acid | Sorbitol | 0.2% | 1/2 water volume separation No oil separation from WIO emulsion |
| Maleic Anhydride | EDA (meda) | Did not dissolve | Wax dropped out of emulsion as solid sludge by 12 hours |
| Acrylic Acid | EDA (aeda) | 0.2% | No water separation from OIW emulsion 1/2 oil separated on top |
| Sorbic Acid | EDA (seda) | Did not dissolve | Same as Control, no wax drop out |
| Acrylic Acid | TEPA (atepa) | Did not dissolve | Same as Control, no wax drop out |
| Sorbic Acid | TEPA (stepa) | 0.2% | 2 mm water separation 1 mm oil separation |
| Maleic Anhydride | Hydroquinone | 0.2% | Same as Control |
| Acrylic Acid | Hydroquinone | 0.2% | Same as Control |
| Sorbic Acid | Hydroquinone | 0.2% | Same as Control |

These data indicate that, at the dosage of study, the products made with sorbitol remain soluble in the MVI 100N and pick up water into a water-in-oil emulsion. This capability at low concentrations is an important to a lubricant detergent/dispersant combination product. These data indicate that the sorbitol esters are the best candidates to act as lubricant dispersant/detergent combinations.

EXAMPLE 1

This example summarizes the data presented herein. Intermediate products with a number of dienes and dienoids with HEAR oil as the exemplary base oil were synthesized to form the resultant intermediate product in three molar ratios. The optimum molar ratio was chosen by testing of the viscosity, viscosity index (VI), acid number, iodine number, solubility, 4-ball wear properties. The molar ratios chosen from these tests were HEAR:maleic anhydride @ 1:0.5, HEAR:acrylic acid @ 1:1, and HEAR:sorbic acid @ 1:0.6.

The anti-wear properties of the sorbic acid/HEAR were the best of the above-noted intermediate products, improving the polyalphaolefin (PAO) base stock by 30%. All the intermediate products were soluble in the three base stocks up to at least 5%.

The intermediate products were further reacted with polar compounds to produce candidate polyol and polyanine products. The intermediate products were esterified with polyols glycerine (three hydroxyls), and sorbitol (six hydroxyls). They were also reacted with ethylenediamine (EDA) and tetraethylene pentamine (TEPA) to form polyamines. The polyols and polyamines were tested for anti-wear properties. They were evaluated for solubility in base stocks and for emulsibility in water as a condition of detergency.

The liquids (polyol esters) and waxes (polyamine amides) that were made were verified by Fourier Transform Infrared (FTIR) Spectrophotometry for chemical structure. All the requisite structures for the expected products were present.

The solubility of the products was altered drastically depending on the polar compound added. Polyamines displayed the lowest solubility problems in all base stocks. The sorbitol esters were the only polyols that had problems dissolving, and then, only, in PAO.

A level of 0.2% of the candidate compounds in MVI 100N was emulsified 50:50 with water and allowed to separate. None of the glycerine esters had an effect on the oil/water separation. The sorbitol esters formed stable water-in-oil emulsions and are candidates for a anti-wear dispersant/detergent compound. The polyamine waxes had solubility problems with oil and produced unstable emulsions.

EXAMPLE 2

This provides a summary of nine compositions made showing each or the tree materials, molar ratios and reaction conditions to illustrate the extent and breadth of the invention. The following Table 5 sumrnarizes these reactions and data.

TABLE 5

| Base Oil | Adduct | Mol Ratio | Esterification/ Amidification Reactants | Adduction | | Product Formation | | |
|---|---|---|---|---|---|---|---|---|
| | | | | Time Min | Temp C | Catalyst | Time Min | Temp C |
| HEAR | Maleic Anhydride | 1:0.5 | Glycerol | 240 | 120 | HPA* | 240 | 160 |
| HEAR | Maleic Anhydride | 1:0.5 | Sorbitol | 240 | 120 | HPA* | 240 | 160 |
| HEAR | Maleic Anhydride | 1:0.5 | Hydroquinone | 240 | 120 | HPA* | 300 | 190 |
| HEAR | Maleic Anhydride | 1:0.5 | Ethylene diamine | 240 | 120 | | 120 | 120 |
| HEAR | Acrylic Acid | 1:1 | Sorbitol | 360 | 170 | HPA* | 240 | 160 |
| HEAR | Sorbic Acid | 1:1 | Ethylene diamine | 360 | 200 | | 120 | 120 |
| HEAR | Sorbic Acid | 1:1 | Tetraethylene penatmine | 360 | 200 | | 120 | 120 |
| HEAR | Acrylic Acid | 1:1 | Hydroquinone | 360 | 170 | HPA* | 300 | 190 |
| HEAR | Sorbic Acid | 1:1 | Hydroquinone | 360 | 200 | HPA* | 300 | 190 |
| SOY | Sorbic Acid | 1:1 | Sorbitol | 360 | 200 | HPA* | 240 | 160 |

*HPA = Hypophosphorus Acid

EXAMPLE 3

This provides a summary of data evaluating various diesel fuel lubricity additives for lubricity, fuel properties, combustion and deposits. Lubricity was measured using an industry standard Scuffing Load Ball on Cylinder (SLBOCLE), ASTM D-6078, and High Frequency Reciprocating Rig (HFRR), ASTM D-6079 tests. The data compare no lubricity additive with three different concentrations of inventive lubricity additive SSS-1.7.7, which is a soy oil-sorbic acid-sorbitol product at 1:1 molar ratios. The data are provided in Table 6.

TABLE 6

| | | | | SSS-1.7.7 | | |
|---|---|---|---|---|---|---|
| FUEL OIL GRADE | TEST | PASSING VALUE | NO ADDITIVE | 2000 ppm | 500 ppm | 100 ppm |
| #1 Diesel Fuel (kerosene) | SLBOCLE | >3100 | 1250 | 5350 | 3650 | 2250 |
| | HFRR | <450 | 675 | 176 | 303 | 656 |
| Source A #2 Diesel Fuel | SLBOCLE | >3100 | 4200 | NT | 5050 | 4100 |
| | HFRR | <450 | 531 | NT | 261 | 500 |
| Source T #2 Diesel Fuel | SLBOCLE | >3100 | 4000 | NT | 5400 | 4875 |
| | HFRR | <450 | 502 | NT | 178 | 222 |

NT denotes Not Tested

In addition, the fuel properties of a diesel fuel containing 500 ppm of the inventive SSS-1.7.7 fuel lubricity additive showed that the fuel properties were not affected by addition of 500 ppm of the inventive fuel lubricity additive.

TABLE 7

| TEST | REFERENCE | 500 ppm SSS 1.7.7 ADDED |
|---|---|---|
| Cetane Number | 47.2 | 47.8 |
| Cold Filter Plugging Point ASTM D | −20 C | −20 C |

An emissions and combustion test was conducted on a 276 CID, John Deere 4276T turbocharged, direct-injected, 4 cylinder diesel engine mounted on a dynamometer. The engine speed and torque output were varied in three sections during the 125 hour test. Any problems with combustion or injector deposits show up as high final values of Hydrocarbons and Carbon Monoxide (CO) and smoke (BSN) in the exhaust. The diesel fuel used had 500 ppm of SSS-1.7.7 added. The data provided in Table 8 show that the fuel with additive did not affect any change in engine operation.

TABLE 8

| TEST CONDITIONS | EMISSIONS | INITIAL | FINAL |
|---|---|---|---|
| Section 1-Peak Torque | CO, ppm | 129 | 101 |
| 1400 RPM | $CO_2$, % | 8.0 | 8.3 |
| 220 ft-lb Torque | Hydrocarbons, ppm $C_6$ | 32.6 | 31.6 |
| | Smoke (BSN) | 1.77 | 1.83 |
| Section 2-Rated Power | CO, ppm | 95 | 85 |
| 2100 RPM | $CO_2$, % | 7.5 | 7.3 |
| 187 ft-lb Torque | Hydrocarbons, ppm $C_6$ | 27.9 | 24.8 |
| | Smoke (BSN) | 0.67 | 0.73 |
| Section 3-Light Load | CO, ppm | 252 | 268 |
| 1200 RPM | $CO_2$, % | 2.9 | 2.1 |
| 30 ft-lb Torque | Hydrocarbons, ppm $C_6$ | 55.9 | 51.2 |
| | Smoke (BSN) | 0.63 | 0.60 |

The values are within experimental error for each of the initial and final readings, indicating little or no change in the engine operation.

A Cummins L-10 deposits test was run with a Cummins 6 cylinder diesel engine in accordance with Cummins Test Method 60032. The fuel used was Howell 0.4% (4000 ppm) Sulfur fuel, the only reference fuel available for the method. (Cummins has not chosen a low-sulfur reference fuel as of this study.) The results of the Cummins L-10 deposit test in Table 9 show that the inventive diesel fuel lubricity additive did not affect the deposit characteristics of the fuel to any significant degree.

TABLE 9

| TEST PARAMETER Change at End of Test | REFERENCE FUEL | REFERENCE FUEL PLUS 250 PPM SSS-1.7.7 |
|---|---|---|
| Average Flow Rate Loss | 6.0% Maximum | 5.8% |
| Average CRC Rating of 6 Injectors | 21.2–28.6 Range | 23.6 |

We claim:

1. A fuel lubricity additive compound, comprising an intermediate adduct of a first moiety reacted in a first reaction with a second moiety to form the intermediate adduct and further esterifying or amidifying the intermediate adduct with a third moiety in a molar ratio of from about 1:2 to about 2:1, wherein the first moiety is a unsaturated triglyceride plant oil or a thermal polymer thereof, wherein the second moiety is a diene or conjugated double bond acid or anhydride moiety, wherein the first reaction comprises mixing the first moiety with the second moiety in a molar ratio of from about 1:2 to about 2:1 at a temperature of from about 130° C. to about 195° C. under an inert atmosphere; and wherein the third moiety is a polyhydroxy compound or a polyamino compound.

2. The fuel lubricity additive of claim 1 wherein the unsaturated plant oil is selected from the group consisting of rapeseed oil, tung oil, linseed oil, soya oil, corn oil, peanut oil, canola oil, safflower oil, or combinations thereof.

3. The fuel lubricity additive of claim 1 wherein the thermal polymer is selected from the group consisting of thermal (telomer) polymers of canola oil, soya oil, linseed oil, corn oil, safflower oil, peanut oil, tung oil, and combinations thereof.

4. The fuel lubricity additive of claim 1 wherein the second moiety comprises unsaturated compounds having a free carboxylic acid or anhydride group.

5. The fuel lubricity additive of claim 4 wherein the second moiety is selected from the group consisting of maleic acid, maleic anhydride, sorbic acid, sorbic anhydride, tetrahydrophthalic anhydride, tetrahydrophthalic acid, salicylic acid, salicylic anhydride, acrylic acid, acrylic anhydride, $C_{1-10}$ alkyl, $C_{2-10}$ alkenyl, or $C_{1-10}$ alkoxy derivatives of the foregoing acids and anhydrides, and combinations thereof.

6. The fuel lubricity additive of claim 1 wherein the polyhydroxy compound of the third moiety is selected from the group consisting of glycerol, sorbitol, hydroxyquinone, glucose, mannose, 6-carbon sugars, pentose, fructose, 5-carbon sugars, pentaerythritol, catechol, resorcinol, hydroquinone, pyrogallol, 4,4'-dihydroxybiphenyl, 2,4-dihydroxybiphenyl, 2,2'-dihydroxybiphenyl, orthohydroxybenzene, polyhydroxyaromatic compounds having one or two phenyl rings and one or two 5–6 membered aromatic rings having substituted alkyl or alkenyl side chains ($C_{2-10}$) substituted with at least two hydroxyl groups, trimethylolpropane, pentaerythritol, dimethylolpropane, dipentaerythritol, trimethylolethane, ethyleneglycol, polypropyleneglycol, polyethylated alcohols, and combinations thereof.

7. The fuel lubricity additive of claim 1 wherein the polyamino compound is selected from the group consisting of diethylenetriamine, dimethylenetriamine, dipropylenetriamine, ethyenediamine, propylenediamine, butylenediamine, butylenetriamine, triethylenetetramine, tripropylenetetramine, trimethylenetriamine, tributylenetetramine, tetraethylenepentamine, tetramethylenepentamine, tetrapropylenepentamine, tetrabutylenepentamine, hexylenediamine, and combinations thereof.

8. The fuel lubricity additive of claim 1 wherein the first reaction is conducted under continuous mixing.

9. The fuel lubricity additive of claim 1 wherein the esterification reaction comprises reaction conditions of from about 150° C. to about 190° C. under an inert atmosphere and further comprises adding an esterification catalyst.

10. The fuel lubricity additive of claim 9 wherein the esterification catalyst is an acid catalyst.

11. The fuel lubricity additive of claim 10 wherein the esterification catalyst is selected from the group consisting of p-toluene sulfonic acid, hydrophosphorous acid, sulfuric acid, hydrochloric acid, phosphoric acid, acid-activated clays, solid acid catalysts, acidic zeolites, and combinations thereof.

12. The fuel lubricity additive of claim 1 wherein the amidification reaction comprises reaction conditions of from about 130° C. to about 150° C. under an inert atmosphere.

13. The fuel lubricity additive of claim 1 wherein the fuel lubricity additive compound is made from the first moiety, second moiety and third moiety compounds selected from the group consisting of in order soya oil-maleic anhydride-sorbitol, soya oil-linseed oil combination-maleic anhydride-sorbitol, soya oil-maleic anhydride-ethylenediamine, and soya oil-maleic anhydride-hydroquinone.

14. A process for synthesizing a fuel lubricity additive compound, comprising
   (a) reacting an unsaturated triglyceride plant oil or a thermal polymer thereof first moiety with a second moiety in a molar ratio of from about 1:2 to about 2:1 at a temperature of from about 130° C. to about 195° C. under an inert atmosphere to form an intermediate adduct, wherein the second moiety is a diene or conjugated double bond acid or anhydride moiety; and
   (b) esterifying or amidifying the intermediate adduct with a third moiety in a molar ratio of from about 1:2 to about 2:1, wherein the third moiety is a polyhydroxy compound or a polyamino compound.

15. The process of claim 14 wherein the unsaturated plant oil is selected from the group consisting of rapeseed oil, tung oil, linseed oil, soya oil, corn oil, peanut oil, canola oil, safflower oil, or combinations thereof.

16. The process of claim 14 wherein the thermal polymer is selected from the group consisting of thermal (telomer) polymers of canola oil, soya oil, linseed oil, corn oil, safflower oil, peanut oil, tung oil, and combinations thereof.

17. The process of claim 14 wherein the second moiety comprises unsaturated compounds having a free carboxylic acid or anhydride group.

18. The process of claim 17 wherein, the second moiety is selected from the group consisting of maleic acid, maleic anhydride, sorbic acid, sorbic anhydride, tetrahydrophthalic anhydride, tetrahydrophthalic acid, salicylic acid, salicylic anhydride, acrylic acid, acrylic anhydride, $C_{1-10}$ alkyl, $C_{2-10}$ alkenyl, or $C_{1-10}$ alkoxy derivatives of the foregoing acids and anhydrides, and combinations thereof.

19. The process of claim 14 wherein the polyhydroxy compound of the third moiety is selected from the group consisting of glycerol, sorbitol, hydroxyquinone, glucose, mannose, 6-carbon sugars, pentose, fructose, 5-carbon sugars, pentaerythritol, catechol, resorcinol, hydroquinone, pyrogallol, 4,4'-dihydroxybiphenyl, 2,4-dihydroxybiphenyl, 2,2'-dihydroxybiphenyl, orthohydroxybenzene, polyhydroxyaromatic compounds having one or two phenyl rings and one or two 5–6 membered aromatic rings having substituted alkyl or alkenyl side chains ($C_{2-10}$) substituted with at least two hydroxyl groups, trimethylolpropane, pentaerythritol, dimethylolpropane, dipentaerythritol, trimethylolethane, ethyleneglycol, polypropyleneglycol, polyethylated alcohols, and combinations thereof.

20. The process of claim 14 wherein the polyamino compound is selected from the group consisting of diethylenetriamine, dimethylenetriamine, dipropylnetriamine, ethyenediamine, propylenediamine, butylenediamine, butylenetriamine, triethylenetetramine, tripropylenetetramine, trimethylenetriamine, tributylenetetramine, tetraethylenepentamine, tetramethylenepentamine, tetrapropylenepentamine, tetraethylenepentamine, tetrabutylenepentamine, hexylenediamine, and combinations thereof.

21. The process of claim 14 wherein the first reaction is conducted under continuous mixdng.

22. The process of claim 14 wherein the esterification reaction comprises reaction conditions of from about 150° C. to about 190° C. under an inert atmosphere and further comprises adding an esterification catalyst.

23. The process of claim 14 wherein the esterification catalyst is an acid catalyst.

24. The process of claim 23 wherein the esterification catalyst is selected from the group consisting of p-toluene sulfonic acid, hydrophosphorous acid, sulfuric acid, hydrochloric acid, phosphoric acid, acid-activated clays, solid acid catalysts, acidic zeolites, and combinations thereof.

25. The process of claim 14 wherein the amidification reaction comprises reaction conditions of from about 130° C. to about 150° C. under an inert atmosphere.

26. A fuel lubricity additive or a dispersant comprising a product of a first and a second reaction, (a) wherein the first reaction is an adduction reaction of a base oil and a dienophile having a carboxylic acid moiety selected from a formula I or a formula III:

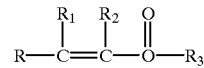

wherein R, $R_1$ and $R_2$ are independently hydrogen, hydroxyl, a straight chain or branched chain $C_{1-12}$ alkyl, $C_{1-12}$ acyl, $C_{1-12}$ aryl, $C_{4-12}$ cycloalkyl, or $C_{1-12}$ alkoxy; and wherein $R_3$ is hydrogen, a straight chain or branched chain $C_{1-12}$ alkyl, $C_{1-12}$ acyl, $C_{1-12}$ aryl, $C_{4-12}$ cycloalkyl, or $C_{1-12}$ alkoxy, or formula II

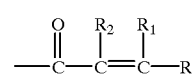

or formula III

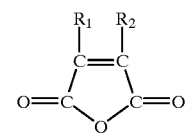

wherein $R_1$ and $R_2$ are the same as in formula I; and (b) wherein the second reaction is an esterifying or an amidifying of the carboxylic acid functional moiety of the aliphatic intermediate product of the first reaction with a polyol compound or polyamino compound having from 2 to 10 free hydroxyl groups and selected from the group consisting of substituted or unsubstituted mono-, di-, tri-, tetra- or penta-sugars, glycerols, glycols, pentaerythrols, and combinations thereof, wherein the substitutions are selected from the group consisting of hydroxyl, oxo, halogen (chloro, bromo, iodo, fluoro), straight chain or branched chain $C_{1-12}$ alkyl, $C_{1-12}$ acyl, $C_{1-12}$ aryl, $C_{4-12}$ cycloalkyl, hydroxyl, and $C_{1-12}$ alkoxy.

27. The fuel lubricity additive of claim 26, wherein the dienoid carboxylic acid is selected from the group consisting of maleic acid, phthalic acid, sorbic acid, acrylic acid, and combinations thereof.

28. The fuel lubricity additive of claim 26, wherein the base oil is selected from the group consisting of HEAR (high erucic acid rapeseed oil), linseed oil, soybean oil, canola oil, telomer oil having a kinematic viscosity of 6000 SUS, and combinations thereof.

29. The fuel lubricity additive of claim 26, wherein the base oil is either a triglyceride (all straight chain) with at least one of the acyl chains being unsaturated, or a straight chain wax ester of from about 18–48 carbons atoms in length and being at least monounsaturated.

30. The fuel lubricity additive of claim 29, wherein the base oil acyl fatty acid chains of the triglyceride are from 3 to 24 carbon atoms in length (straight) and have from one to three double bonds.

31. The fuel lubricity additive of claim 30, wherein the base oil unsaturated fatty acid acyl chains have from 10–24 carbons atoms.

* * * * *